United States Patent [19]

Dal Pozzo et al.

[11] Patent Number: 5,264,425
[45] Date of Patent: Nov. 23, 1993

[54] GLYHCOSAMINOGLYCAN SALTS AND PHARMACEUTICAL COMPOSITIONS CONTAINING THEM

[75] Inventors: Alma Dal Pozzo; Maurizio Acquasaliente; Giancarlo Sportoletti; Monique Sarret; Paolo Ferruti; Francesco De Santis, all of Milan, Italy

[73] Assignee: Italfarmaco S.p.A., Milan, Italy

[21] Appl. No.: 623,378

[22] PCT Filed: May 30, 1989

[86] PCT No.: PCT/EP89/00605

§ 371 Date: Nov. 15, 1990

§ 102(e) Date: Nov. 15, 1990

[87] PCT Pub. No.: WO90/12589

PCT Pub. Date: Nov. 1, 1990

[30] Foreign Application Priority Data

Jun. 3, 1988 [IT] Italy ................. 20854 A/88
May 24, 1989 [IT] Italy ................. 47985 A/89

[51] Int. Cl.$^5$ ............... A61K 31/725; A61K 31/73; C07C 69/96; C08B 37/10
[52] U.S. Cl. ............... 514/54; 514/56; 514/572; 514/589; 514/613; 514/642; 514/643; 536/21; 536/54; 536/55; 558/276
[58] Field of Search ............... 514/54, 56, 589, 613, 514/642, 643, 572; 536/21, 54, 55, 55.3; 558/276

[56] References Cited

U.S. PATENT DOCUMENTS

| | | | |
|---|---|---|---|
| 2,830,932 | 4/1958 | Cushing et al. | 536/21 |
| 3,162,673 | 12/1964 | Brotherton et al. | 558/276 |
| 3,244,594 | 4/1966 | Csaba et al. | 536/21 |
| 4,324,739 | 4/1982 | Zondler et al. | 558/445 |
| 4,352,913 | 10/1982 | Zondler et al. | 528/365 |
| 4,478,822 | 10/1984 | Haszam et al. | 514/56 |
| 4,506,081 | 3/1985 | Fenyes et al. | 544/372 |
| 4,510,135 | 4/1985 | Teng | 514/56 |
| 4,581,058 | 4/1986 | Fenyes et al. | 544/357 |
| 4,591,638 | 5/1986 | Ahrgren et al. | 536/112 |
| 4,604,376 | 8/1986 | Teng | 514/56 |
| 4,654,327 | 3/1987 | Teng | 536/21 |
| 4,703,042 | 10/1987 | Bodor | 574/56 |
| 4,727,063 | 2/1988 | Naggi et al. | 514/56 |
| 4,783,447 | 11/1988 | Del Bono et al. | 514/56 |
| 4,910,142 | 3/1990 | Schwengers et al. | 536/55.1 |
| 4,981,955 | 1/1991 | Lopez | 536/21 |
| 4,985,410 | 1/1991 | Conti | 514/54 |

FOREIGN PATENT DOCUMENTS

| | | |
|---|---|---|
| 0676310 | 12/1963 | Canada . |
| 0017623 | 10/1980 | European Pat. Off. . |
| 3020220 | 12/1981 | Fed. Rep. of Germany . |
| 2021042 | 7/1970 | France . |
| 0768524 | 2/1957 | United Kingdom . |
| 2126579 | 3/1984 | United Kingdom . |
| 2176200 | 12/1986 | United Kingdom . |

OTHER PUBLICATIONS

Tadolini et al; Chem. Ab. 99:209189g (1983).
Tadolini et al; Chem. Ab. 101:35516d (1984).
Tadolini et al; Chem. Ab. 103:192661f (1985).
Ehrenpreis et al; Biochim. Biophys. Acta 44:577-585 (1960).

Primary Examiner—Nancy S. Husarik
Attorney, Agent, or Firm—Griffin Butler Whisenhunt & Kurtossy

[57] ABSTRACT

Salts of glycosaminoglycans (heparin, its fractions or fragments which are supersulfated, dermatan sulfate, heparan sulfate, and modified heparins) with bases of formula (I),

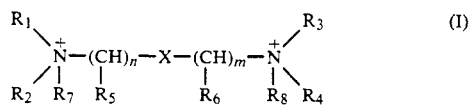

wherein $R_1$, $R_2$, $R_3$, and $R_4$ represent H, alkyl, or cycloalkyl; $R_5$ and $R_6$ represent H, or alkyl; $R_7$ and $R_8$ represent H or alkyl; n and m are integers from 1–4 and X is $-O-CO-O-$, which salts have the pharmacological properties of the glycosaminoglycans themselves, and are orally and rectally administrable.

10 Claims, No Drawings

GLYHCOSAMINOGLYCAN SALTS AND PHARMACEUTICAL COMPOSITIONS CONTAINING THEM

The present invention refers to glycosaminoglycan salts which are able to induce therapeutically effective blood levels of the glycosaminoglycanic polyanion even when administered orally or rectally.

Proteoglycans are macromolecules characterized by a proteic core to which different polysaccharides are covalenty bound. They differentiate by the nature of the proteins and that of the saccharidic side chains and constitute the major part of some mammalian tissues.

By suitable hydrolytic methods (e.g. by means of proteases) it is possible to separate the proteic part from the saccharidic part, commonly known as glycosaminoglycans, because of their content in aminosugars.

The glycosaminoglycans known as chondroitin-4- or 6-sulfate, heparan sulfate, heparin, dermatan sulfate, hyaluronic acid etc., are characterized, in each single family, by polydispersion of molecular weight and also by heterogenity in the saccharidic compositions, and are thus obtained, also industrially.

Due to their highly hydrophilic, polyanionic nature, glycosaminoglycans are able to interact with various chemical species, such as divalent cations or plasmatic basic proteins, often aspecifically and sometimes (such as in the case of the heparin - anti-thrombin III complex or of the dermatan sulfate - cofactor III complex) with a certain specificity, whose degree is higher or lower according to the ligand or to the binding agent.

Interactions occur also with chemical species bound to cell membrane structures such as those constituting the blood vessels.

Due to said interactions, glycosaminoglycans are interesting therapeutic agents, because they allow to control of pathological conditions wherein either the activation or the inhibition of certain plasma factors (such as anti-thrombin III or the activated factor X) are highly useful.

The glycosaminoglycans used for the preparation of the salts of the invention are the following:
unfractionated heparin, which is not dependent on the nature of the extractive source (porcine, bovine or ovine intestinal mucosa, lung etc.) or on the extraction and purification methods;
heparinic fractions and fragments, of any molecular weight and anionic charge value, which is not dependent on the preparation and isolation methods;
heparins, fractions or fragments as above, subjected to further sulfatation operations ("supersulfated");
dermatan sulfate, its fragments or fractions, and also supersulfated;
heparan sulfate, its fragments or fractions, and also supersulfated;
modified heparins, with different molecular weights, obtained by N-desulfation (10–100%) of heparins and then subjected to hemisuccinylation.

Heparin is extracted from tissues of different origin: bovine or porcine intestinal mucosa, lung etc. Chemically heparin, as well as its fractions or fragments, is a mixture having polydispersed molecular weight ranging from 1,000 to 30,000 D.

Under the biological profile, heparin itself, its fragments and fractions show different pharmacological activities, particularly anticoagulant, anti-thrombotic, antiangiogenetic and antilipemic activities. Said activities are connected with the ability of developing interactions with different factors either plasmatic or extraplasmatic (anti-thrombin III, activated factor X, heparin cofactor II, plasminogen activator, lipoproteinlipase in addition to platelet factors) According to the use of heparin as such or of its fragments or fractions (having low molecular weight: 3500–9000 D), one mechanism of action may overcome another one or prolonged or decreased pharmacokinetics may result.

The salts of these polyanions most frequently used in human therapy are the sodium, calcium or magnesium salts.

Dermatan sulfate may be obtained from mammalian tissues such as skin, bowels, tendons etc. by means of enzymatic and controlled chemical hydrolysis.

It is also known as chondroitin sulfate B and shows an anti-thrombotic activity unrelated to the anticoagulant activity, so as to be considered a therapeutic agent safer than heparin. The anti-thrombotic activity seems to be due, according to the present knowledge, to the ability of catalyzing the reaction between heparin - cofactor III and thrombin with consequent inactivation of the latter.

Also for said polyanion the used salts are the sodium and calcium salts.

Heparan sulfate is obtainable from connective tissues such as lungs, basal membranes, walls of blood vessels, pancreas etc.

Even though exhibiting poor in vitro pharmacological activities, it has in vivo a positive anti-thrombotic effect. Also for said polyanion the used salt is an inorganic salt, such as sodium, calcium or magnesium salts.

A particular family of glycosaminoglycans is that of the "supersulfated" derivatives, obtained by sulfation of the above reported different products (having or not having low molecular weight), disclosed in EP 116801. Said derivatives are endowed with low anticoagulant activity, average anti - Xa activity and an anti-thrombotic activity comparable to that of the starting glycosaminoglycan. Also in this case the used form of the salt is the sodium or calcium salt.

Another family of chemically modified glycosaminoglycans is that obtained by controlled N-desulfation (with more or less high N-desulfation degrees) and subsequent succinylation, as disclosed in Italian patents N. 1,140,999 and 1,169,888 and in U.S. Pat. No. 3,118,816.

Said derivatives, in form of sodium or calcium salts, show a reduced anticoagulant activity and good lipasemic and anti-thrombotic activities.

The inorganic salts of the above mentioned glycosaminoglycans may be administered in form of suitable formulations by the systemic route (intravenously, by infusion, subcutaneously etc.) to experimental animals and to humans, showing a marked anti-thrombotic action (particularly venous), which is not noticed when their administration is carried out by the oral route, because of an insufficient bioavailability of the active principles.

Said insufficient oral absorption involves a remarkable limitation for the preventive therapies, carried out for long periods.

In order to overcome this drawback, in recent years different approaches have been carried out. In one approach, the inorganic salts are carried in suitable pharmaceutical compositions comprising different substances (such as, for instance, those reported in: Italian patent application 22010 A/82; Japanese patent 0054-313; EP-A-130550; DE A-3,331.009; U.S. Pat. No. 4,604,376; or by forming complexes (such as in U.S. Pat. No. 4,654,327; U.S. Pat. No. 4,478,822; U.S. Pat. No. 4,510,135), consisting of ammonium derivatives of ethylene oxide and propylene oxide copolymers or of triglycerides; or by the formation of "ion multiplets" consisting of amine or quaternany ammonium derivatives of polyalcohols (PCT/U.S.85/00846).

Nowdays, however, neither oral nor rectal formulations of glycosaminoclycans for the therapy of thrombosis are commercially available.

It has now been surprisingly found that, using as salifying bases—instead of sodium or calcium—organic cations of particular chemical composition, the pharmacological properties typical of said glycosaminoglycans, when administered parenterally, are maintained when the organic salts of the present invention are administered by the oral or rectal route. This effect is also obtained when the salts are prepared by salifying only partially the glycosaminoglycan acid with the above organic bases, the remaining acid groups being in form of inorganic salts (sodium, calcium, magnesium etc.). The organic cations used according to the invention have the general formula I

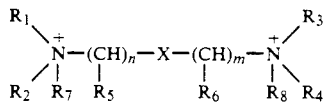

wherein:

R$_1$, R$_2$, R$_3$ and R$_4$, which are the same or different, represent hydrogen; linear or branched alkyl; cycloalkyl; aralkyl; or R$_1$ and R$_2$, respectively R$_3$ and R$_4$, together with the nitrogen atom to which they are bound, form a 5 - or 6 - membered heterocyclic ring optionally containing other hetero atoms;

R$_5$ and R$_6$, which are the same or different, represent hydrogen, C$_1$-C$_4$ alkyl or aryl;

R$_7$ and R$_8$, which are the same or different, represent hydrogen or C$_1$-C$_4$ alkyl;

n and m, which are the same or different, are integers 1 to 4 inclusive;

X represents one of the following groups:

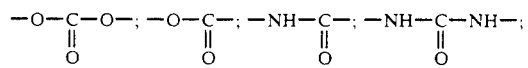

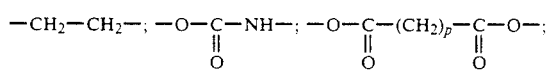

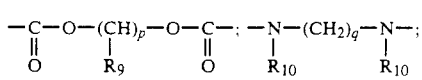

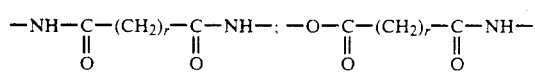

wherein R$_9$ and R$_{10}$ represent hydrogen or C$_1$-C$_4$ alkyl, whereas p is an integer 1 to 6 inclusive;
q is an integer 1 to 4 inclusive;
r is an integer 1 to 5 inclusive.

The present invention also relates to the corresponding bases of the cations of formula I as well as to the inorganic or organic acid salts thereof (such as, for example, the hydrohalogen, sulfuric, phoshoric, carbonic, nitric, formic, acetic, oxalic, maleic, citric, tartaric acids), to the processes for the preparation of the salts of cations I with glycosaminoglycan polyanions; to the pharmaceutical compositions containing one or more salts of glycosaminoglycans with the cations of formula I.

According to the invention, the bases of formula Ia

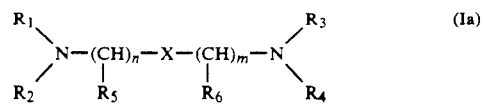

(wherein R$_1$-R$_6$, X, n and m have the above mentioned meanings), corresponding to the cations of formula I in which R$_7$ = R$_8$ = hydrogen, are prepared by means of the methods traditionally used to obtain dialkylcarbonates, carboxylic acid esters, ureas, carbamates, dicarboxylic acid esters or diol esters, diamides, ester-amides and the like. Particularly, where X is —O—CO—O, R$_1$ = R$_3$ and R$_2$ = R$_4$ (i.e. R$_1$ and R$_2$, respectively R$_3$ and R$_4$ form together with the respective nitrogen atom two equal heterocyclic rings), the corresponding aminoalcohols are reacted with phosgene in an about 2:1 molar ratio, in inert solvents such as arenes or ethers or halogenated hydrocarbons, at temperatures from −10° to +30° C., preferably at about 0° C. The reaction mixture is shaken with an aqueous solution of sodium or potassium hydrogencarbonate or carbonate sufficient to neutralize the formed hydrochloric acid; the organic phase is dried and evaporated to dryness.

The obtained products, generally in form of oils, are optionally purified by chromatography. Alternatively, phosgene can be replaced by N,N'-carbonyldiimidazole; in this instance the reaction is carried out in the presence of small amounts of the sodium aminoalkoxide previously prepared by reacting metal sodium with the aminoalcohol, at temperatures from 0° to 50° C., preferably at room temperature. In this case the product is recovered by washing the organic solution with water only.

On the contrary, when

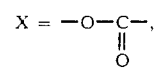

n >1 and m >1, an aminoalcohol

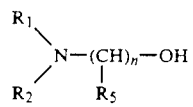

(wherein R$_1$, R$_2$, R$_5$ have the above mentioned meanings), is reacted with an α,β-unsaturated acid reactive derivative, for example the chloride or the anhydride, to obtain the corresponding α,β-unsaturated aminoalkyl ester. The reaction is suitably carried out in inert solvents (halogenated hydrocarbons, arenes, ethers) and in the presence of a tertiary base (triethylamine, pyridine) as the acid binding agent. The resulting ester is then reacted with a R$_3$R$_4$NH amine excess, at temperatures from 0° to 40° C., preferably at room temperature, to obtain the addition of the same amine to the reactive double bond.

Recovery is carried out according to a per se known method.

When X is again a —O—CO— group and n is 1, first a $R_1R_2NH$ dialkylamine is reacted with an $R_5$—CHO aldehyde, in the presence of potassium carbonate, in aqueous medium and at room temperature. The reaction product ($R_1R_2NH$—$CHR_5$—OH) is extracted with a water unmiscible solvent and reacted with an amino acid of formula

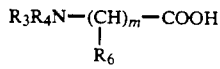

in the presence of dicyclohexylcarbodiimide and pyridine, at temperatures of 0°-50° C., preferably at room temperature. Dicyclohexylurea is filtered off, then the product is recovered by evaporating the solvent and it is purified by chromatography, if necessary.

When in general formula Ia X is the —NH—CO— group and m is higher than 1, a $R_1R_2N$—($CHR_5$-$)_n$—$NH_2$ diamine is acylated with an $\alpha,\beta$-unsaturated acid chloride or mixed anhydride; the obtained amide is then treated with an excess of the $R_3R_4NH$ amine which is added to the reactive double bond. The two procedures can also be reversed. The reaction conditions are similar to the above indicated ones.

When

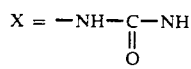

the process is carried out as already indicated for bases Ia in which

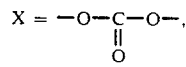

the only difference consisting in the use of diamines instead of aminoalcohols. Analogously, the reaction is carried out to obtain compounds Ia in which

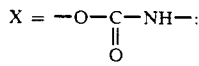

an appropriate dialkylamino-alkylaminocarbonyl chloride is reacted with an appropriate dialkylaminoalcohol.

Compounds Ia wherein

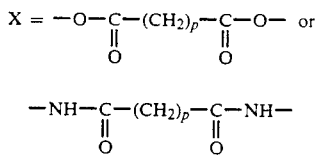

on the contrary, are prepared by reacting appropriate aminoalcohols (respectively appropriate diamines) with alkanedioic acid reactive derivatives, under the conventionally used conditions.

The compounds in which X is the

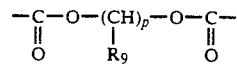

group (wherein $R_9$ and p have the above mentioned meanings) can be prepared from the corresponding diols

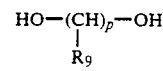

or from reactive derivatives of appropriate aminocarboxylic acids, under the usual conditions for this kind of reactions.

Finally, the cations of formula I in which $R_7$ and $R_8$ are $C_1$-$C_4$ alkyl are suitably obtained by reacting the corresponding bases Ia with the compounds of formula $R_7$-Y ($R_8$-Y), wherein Y is a leaving group, such as chlorine, bromine, iodine, methylsulfonyloxy, tosyloxy. Alternatively, the above described processes can be applied with no particular difficulties to intermediates of the kind:

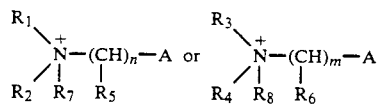

wherein $R_7$ and $R_8$ are different from hydrogen and A is a protected hydroxy or amino group.

The salts of glycosaminoglycan polyanions and the cations of formula Ia, according to the invention, can be obtained:

a) by subjecting aqueous solutions of glycosaminoglycan sodium and calcium salts to chromatography on resins, at T<7° C., to partially or completely remove sodium and calcium ions. The eluates are treated either with bases Ia or with hydroxides of the cations I, in which $R_7$ and $R_8$ are $C_1$-$C_4$ alkyl, in the desired stoichiometric ratio, to obtain either "neutral" salts or salts still containing an anion excess, which possibly can be neutralized with different cations, or a cation excess which can be neutralized with different anions;

b) by subjecting to diafiltration aqueous solutions of glycosaminoglycans sodium salts and of salts of the cations of formula I with inorganic acids, particularly hydrohalogen acids.

In both cases the final salt is suitably recovered by freeze-drying.

The following non-limiting Examples further illustrate the invention.

Preliminary Remarks

In the examples hereinafter, the following glycosaminoglycans and derivatives thereof and the following tests were used:

1. Glycosaminoglycans (GAG):
   1.1. Sodium heparin, from pig, of molecular weight about 13,500 D. Anti-Xa activity 175 units/mg (chromogens). Anti-coagulant activity: 170 I.U./mg (PRODUCT P1).
   1.2. Low molecular heparin, sodium salt, average molecular weight about 4,000 D. Anti-Xa activity:

95 units/mg (chromogens). Anti-coagulant activity: 58 I.U./mg (PRODUCT P2).

1.3. Sodium dermatan sulfate, average molecular weight about 20,000 D. Anti-coagulant activity: 45 I.U./mg (PRODUCT P3).

1.4. Sodium heparan sulfate, average molecular weight about 18,500 D. Anti-Xa activity: 72 units/mg (chromogens). Anti-coagulant activity: 20 I.U./mg (PRODUCT P4).

1.5. Supersulfated heparin fragments obtained as described in the above cited E.P. n. 116801. Average molecular weight about 6,000 D. Anti-Xa activity: 60 units/mg (chromogens). Anti-coagulant activity: 15 I.U./mg (PRODUCT P5).

The use of GAG having the above reported chemico-physical and biological characteristics to illustrate the present invention is not to be intended to limit the scope of the invention itself, which also applies to those GAG having different molecular weights, salifications and biological activities from the exemplified ones, which are typical of the commercially available GAG. 2. Tests 2.1. In vitro determination of the anticoagulant activity (USP units: according to United States Pharmacopoeia XIX, sheep plasma).

2.2. In vitro determination of anti-Xa activity: (according to Teien et al., Thrombosis Research Vol 8, 413, 1976), chromogenic method with S-2222 substrate (COATEST$^R$).

2.3. Absorption evaluation by determination of anti-Xa activity of glycosaminoglycans such as heparan, low molecular weight heparin and heparan sulfate.

The used method consists in the ex vivo evaluation of the factor Xa inhibition after intraduodenal administration in the rat, rabbit or dog of the compound under examination in comparison with the starting glycosaminoglycan salified with inorganic ions (sodium, calcium). The used determination method is the above described chromogenic method (COATEST$^R$); it provides spectrophotometric values which are converted into blood concentrations (mcg/ml) of glycosaminoglycans, obtained by comparison with a calibration curve calculated with the same glycosaminoglycan in the form of the sodium salt, added in vitro to the plasma. Said calibration curve is obtained for each kind of used glycosaminoglycan.

2.4. Evaluation of the in vivo antithrombotic activity for the glycosaminoglycans not endowed with anti-Xa activity, such as dermatan sulfate, after intraduodenal administration in the rat (thrombosis model of Reyers et al.—Thromb. Res. Vol. 8, 669, 1980, consisting in the ligation of the lower vena cava in order to induce stasis and then thrombosis). The used parameter is the percent inhibition of the thrombus formation.

EXAMPLE 1

Preparation of bis-N,N-dialkylamino-alkylene carbonates (X: —O—CO—O—)

A flask containing 500 ml of toluene was weighted, then ice-cooled; gaseous phosgene was slowly bubbled therein (for about 1 hour) until the weight corresponding to 0.55 mole was reached. N,N-dialkylamino-alcohol corresponding to the desired final product (1 mole) was added under stirring at 0° C. and the solution was left- to stand for 2 hours; then it was shaken with a cool diluted aqueous solution of 0.58 mole of $K_2CO_3$, then with water, finally it was dried over $Na_2SO_4$. Solvent was evaporated off to leave residues consisting of the final products in form of pale yellow or colorless oils, in 90% average yields. The products can be purified from any traces of the starting reactives by column chromatography (silica gel 60, 70–230 mesh, eluent: benzene/tetrahydrofuran 60:40). The chemico-physical characteristics of some of this series of products are exemplified in Table 1 (in which $R_1$, $R_2$, $R_3$ and $R_4$ groups are equal to each other, whereas in compound n. 5 the $R_1$ and $R_2$, respectively $R_3$ and $R_4$ groups, form a piperidine ring with the nitrogen atom to which they are bound).

EXAMPLE 2

Preparation of bis-N,N-dialkylamino-alkylene carbonates (X: —O—CO—O—)

To a solution of the suitably selected aminoalcohol (1 mole in 250 ml of tetrahydrofuran) sodium metal (0.05 mole) was added and left to slowly dissolve therein at room temperature (for some hours) The mixture was diluted with 250 ml more of tetrahydrofuran and N,N-carbonyl-diimidazole (0.55 mole) was added, under cooling, if necessary, to maintain the reaction mixture to room temperature. After 1 hour stirring, the solvent was removed under vacuum and the residue was taken up into chloroform until complete dissolution. The chloroform solution was washed with the same volume of water and evaporated to dryness to obtain an oily residue consisting of the final product, in an about 95% yield on theory. The final product can further be purified by chromatography, as described in Example 1.

EXAMPLE 3

Preparation of bis-N,N dialkylamino-alkylene esters (X: —O—CO—; both n and m >1)

An N,N-dialkylamino-alcohol corresponding to the desired final product (0.05 mole) and triethylamine (0.55 mole) were dissolved in 500 ml of anhydrous methylene chloride. The solution was cooled to 0°-5° C., said temperature being maintained during the whole reaction time. 0.55 mole of acryloyl chloride dissolved in 150 ml of methylene chloride was slowly added to the reaction flask, under stirring. At the end of the addition the reaction was left to proceed until completion for 1 hour, under stirring. The mixture was filtered and the filtrate was washed with water (2×150 ml), with a sodium hydrogencarbonate saturated solution (2×150 ml), then with water (2×150 ml); the organic phase was then dried and the solvent was removed under vacuum. The residue consisted of N,N-dialkylamino alcohol acrylate, in a 90% yield. This residue was taken up into 1 liter of the corresponding N,N-dialkylamine and left at room temperature for 18 hours under stirring. The secondary amine excess was removed by distillation under vacuum (suitably at 30° C. and 16 mm Hg) and the residue was taken up into 1 liter of acetonitrile; solvent was removed under vacuum (at 30° C). The process was repeated several times until complete elimination of any traces of the free amine. The residue was the final pure product, which was in form of a slightly yellow oil (100% yield). The chemico physical characteristics of some derivatives from said series are reported in Table 1.

EXAMPLE 4

Preparation of bis-N,N-dialkylamino-methylene esters
(X = —O—CO—; n = 1; m ≧ 1)

The N,N-dialkylamine corresponding to the desired final product (0.5 mole) and potassium carbonate (0.05 mole) were suspended into 1 liter of distilled water at was added under strong stirring to the suspension, which was reacted for 24 hours. After that, the crude product was extracted with chloroform, washing then the chloroform solution with the appropriate water amount (Solution A).

At the same time dialkyl-glycine, corresponding to the desired final product (0.5 mole) was dissolved in 500 ml of chloroform with pyridine (0.5 mole) and dicyclohexylcarbodiimide (0.5 mole) was added to the solution; the mixture was kept under stirring at room temperature for 1 hour (Solution B).

Then Solution A was added to Solution B and the mixture was kept under stirring at room temperature for a night. Then it was filtered and solvent was evaporated off under vacuum. The final products can be purified from any traces of the starting materials by column chromatography, as described in Example 1. Average yield: 70%.

EXAMPLE 5

N,N-dialkylamino-alkylene amides (X: —HN—CO—; m ≧ 1)

The N,N-dialkylamino-amine corresponding to the desired final product (0.5 mole) and triethylamine (0.55 mole) were dissolved in 500 ml of anhydrous methylene chloride. The solution was cooled to 0°-5° C. and a solution of acryloyl chloride (0.55 mole) in 150 ml of methylene chloride was slowly added, under stirring, keeping temperature at about 0° C. After that the mixture was kept under stirring for 1 hour, then it was filtered and the filtered solution was washed with water, with a saturated hydrogencarbonate solution, then again with water; then the procedure described in Example 3 was carried out.

The residue, N,N-dialkylamino-alkylene-acrylamide was obtained in a 95% yield. The transformation into the desired N,N-dialkylamino-alkylene-amides (in quantitative yields) takes place as described in Example 3.

In table 1 the properties of some derivatives from said series are reported.

EXAMPLE 6

Preparation of bis-N,N dialkylamino-alkylene-ureas (X: —HN—CO—NH—)

The procedure of Example 1 was followed, starting from the corresponding N,N-dialkylamino-amines. Yields of 95-100% on theory. The chemico-physical characteristics of some derivatives from this series are reported in Table 1.

EXAMPLE 7

Preparation of bis-N,N-dialkylamino-alkylene-ureas (X: —HN—CO—NH—)

The procedure of Example 2 was followed, using N,N-dialkylamino-amines instead of the corresponding amino-alcohols. Yields of 95-100% on theory.

EXAMPLE 8

Salification of Heparin (P1) with Bis-N,N-Dibutyl-Ethylene Carbonate (Table 1: Base 2; Table 2: Salt 2a), by Direct Salification of the Glycosaminoglycan Acid An aqueous solution containing 7.0 g of the heparin described in item 1.1. of the Preliminary Remarks (Product P1) was percolated through a column containing 50 ml of the cationic resin Dowex 50W×8, maintained at 4° C., recovering the eluate together with the washings into a vessel maintained at 4° C. The cooled solution was promptly neutralized with 6.23 g of bis-N,N-dibutyl-ethylene-carbonate (2). Then the solution was freeze-dried and the heparin salt 2a was obtained in form of a white powder.

According to the same procedure, the salts of all the bases and glycosaminoglycans described in the Preliminary Remarks (Products: P1, P2, P3, P4 and P5) were obtained.

In Table 2 the chemico-physical characteristics of 2a, together with the ones of other salts of glycosaminoglycans P1, P2, P3, P4, P5 and other bases, obtained by the same method, are reported.

EXAMPLE 9

Salification of Low Molecular Weight Heparin (P2) with Bis-N,N-Dihexyl-Ethylene-Carbonate (Table 1; Base 4; Salt 4b), by Direct Salification of the Glycosaminoglycan Acid An aqueous solution containing 7.0 g of heparin, as described in Example 8, was percolated through a column containing 50 ml of the cationic resin Dowex 5W ×6, maintained at 4° C., recovering the eluate together with the washings into a vessel containing 9.05 g of bis-N,N-dihexyl-ethylene-carbonate, maintained at 4° C.

The suspension initially at pH 5, was stirred till complete neutralization (60 minutes). Then the suspension was freeze-dried and the heparin salt 4b was obtained.

According to the same procedure, the salts of all the bases and glycosaminoglycans P1, P2, P3, P4 and P5 were obtained.

In Table 2 the chemico-physical characteristics of 2b, together with the ones of other salts of glycosaminoglycans P1, P2, P3, P4, P5 and other bases obtained in the same manner are reported.

EXAMPLE 10

Salification of Heparin (P1) with Bis-N,N-Dibutyl-Ethylene-Carbonate (Table 1: Base 2; Table 2: Salt 2a) by Shifting the Salification Equilibrium with Membranes 7 g of heparin (product P1, item 1.1 of the Preliminary Remarks) were dissolved in 50 ml of distilled water and 7 g of bis-N,N-dibutyl-ethylene-carbonate (2) were added thereto, in a continuous diafiltration system provided with a cellulose acetate membrane (or polyester, teflon, polyamide or polyurethane membrane) with cut-off from 200 to 1,000 D (preferably 600 D): when 200 ml of dialfiltration product were reached, further 7 g of bis-N,N-dibutyl-ethylene-carbonate were added and diafiltration was repeated until absence of sodium in the diafiltrate. The salt (2a, Table 2) obtained by freeze-drying, shows the same characteristics of the one described in Example 7.

According to the same procedure, the salts of the bases with glycosaminoglycans P1, P2, P3, P4 and P5 were obtained, some examples of which are reported in Table 2.

EXAMPLE 11

In Table 3, the results of the inhibition of the Xa factor, as reported in point 2.3 of the Preliminary Remarks, used as absorption index (in the Table the salts are referred to with the same abbreviations reported in the Table 2) are shown.

The amounts of the administered salts in aqueous solutions (with the exclusion of 4b and 4a administered in suspension of polyethyleneglycols, PEG), reported in the Table, are expressed as mg/kg of body weight and correspond to about 50 mg/kg of salified glycosaminoglycan (conventional heparin; low molecular weight heparin; heparan sulfate; supersulfated, low molecular weight heparin).

The plasma levels are detected at 30' from the administration and are expressed as mean value ± E.S. (animals: S.D. Charles River rats, weighing about 300 g, fasted, 5 animals per group, under anesthesia; or N.Z. rabbits coming from Bettinardi, about 2 Kg weight, fasted, under anesthesia, 3 animals per group).

As it may be evidenced from Table 3, the absorptions are 1.4 to 450 times higher than those of the corresponding glycosaminoglycan (for the P4 derivative the absorption is considered zero since, under the used experimental conditions, it could not be dosed in a statistically certain way). Said absorptions may be improved using suitable carriers instead of the aqueous solution, as the data reported in Table 3 show, wherein the products are administered in oily suspension (migliol$^R$: 1 ml/kg) at the same doses.

EXAMPLE 12

The derivatives reported in Table 4 are administered, under the same experimental conditions above reported, at the doses shown in the Table. After 30' from the administration, the plasma values are determined as above described in item 3 of the Preliminary Remarks.

EXAMPLE 13

The derivatives in Table 5 are administered i.d. as described in item 2.3 of Preliminary Remarks, at the doses shown and the plasma levels, through the Xa factor inhibiting activity, are determined at different times. The results are shown in Table 5.

EXAMPLE 14

The derivative 2a has been administered i.d. in the dog with duodenal fistula at the dose of 100 mg/kg. Beagle dogs coming from Allevamento Alserio weighing 10-12 kg (3 animals/group) have been used. In the Table 6, the heparin plasma levels, measured as described in item 2.4, at different times after the i.d. treatment, are reported.

EXAMPLE 15

The organic salts obtained from the products P3 and P5 (items 1.3 and 1.5 of the Preliminary Remarks) have been tested in the model described in items 2.4 in terms of inhibiting activity of the formation of the thrombus by stasis. In the Table 5, the percent inhibitions for the single salts (referred to as in Table 2) administered by the intraduodenal route 30' before ligation of the vena cava, at the doses hereinbelow reported, corresponding to 50 mg/kg of the product P3, are shown.

The thrombus evaluation is carried out after a two-hours stasis.

10 rats per group (S.D., 250 g body weight), fasted and under anesthesia, have been used. The results are reported in Table 6.

TABLE 1

Chemico-physical characteristics of some bases of general formula Ia general formula

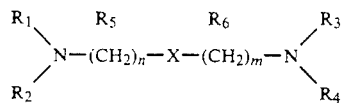

| N | X | n = m | | 1H-NMR(CDCL$_3$, ppm) |
|---|---|---|---|---|
| 1 | carbonate (—O—CO—O—) | 2 | methyl | 4.25(t); 2.62(t); 2.3(s) |
| 2 | carbonate (—O—CO—O—) | 2 | butyl | 4.2(t); 2.75(t); 2.5(t); 1.55–1.1(m); 0.95(t) |
| 3 | carbonate (—O—CO—O—) | 2 | ethyl | 4.2(t); 2.8–2.47(m); 1.05(t) |
| 4 | carbonate (—O—CO—O—) | 2 | hexyl | 4.2(t); 2.75(t); 2.5(t); 1.5–1.1(m); 0.9(t) |
| 5 | carbonate (—O—CO—O—) | 2 | piperidyl | 4.27(t); 2.64(t); 2.45(t); 1.74–1.3(m) |
| 6 | carbonate (—O—CO—O—) | 3 | ethyl | 3.93(t); 2.26(t); 2.25(q); 1.55(quintet); 0.76(t) |
| 7 | carbonate (—O—CO—O—) | 3 | butyl | 4.2(t); 2.63–2.3(m); 1.8(quintet); 1.55–1.1(m); 0.92(t) |
| 8 | carbonate (—O—CO—O—) | 3 | hexyl | 4.15(t); 2.52(t); 2.32(t); 1.76(quintet); 1.40–1.07(m); 0.83(t) |
| 9 | carbonate (—O—CO—O—) | 4 | ethyl | 3.97(t); 2.23(t); 2.20(q); 1.62–1.07(m); 0.78(t) |
| 10 | carbonate (—O—CO—O—) | 4 | butyl | 4.03(t); 2.30(t); 2.27(t); 1.64–1.09(m); 0.80(t) |
| 11 | carbonate (—O—CO—O—) | 4 | hexyl | 4.07(t); 2.48(t); 2.29(t); 1.60–1.10(m); 0.81(t) |
| 12 | ester (—CO—O—) | 2 | methyl | |
| 13 | ester (—CO—O—) | 2 | butyl | 4.14(t); 2.95–2.3(m); 1.55–1.2(m); 0.93(t) |
| 14 | ester (—CO—O—) | 1 | butyl | |
| 15 | ester (—CO—O—) | 2 | hexyl | |
| 16 | ester (—CO—O—) | 2 | octadecyl | |
| 17 | ester (—CO—O—) | 3 | methyl | |
| 18 | ester (—CO—O—) | 3 | butyl | |
| 19 | ester (—CO—O—) | 4 | methyl | |
| 21 | ester (—CO—O—) | 4 | butyl | |
| 21 | amide (—CO—NH—) | 2 | methyl | |
| 22 | amide (—CO—NH—) | 2 | butyl | 3.32(q); 2.8–2.3(m); 1.65–1.2(m); 0.95(t) |

TABLE 1-continued

Chemico-physical characteristics of some bases of general formula Ia general formula

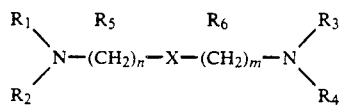

| N | X | n = m | | 1H-NMR(CDCL$_3$, ppm) |
|---|---|---|---|---|
| 23 | amide (—CO—NH—) | 2 | hexyl | |
| 24 | amide (—CO—NH—) | 2 | octadecyl | |
| 25 | amide (—CO—NH—) | 3 | methyl | |
| 26 | amide (—CO—NH—) | 3 | butyl | |
| 27 | amide (—CO—NH—) | 4 | ethyl | |
| 28 | amide (—CO—NH—) | 4 | butyl | |
| 29 | urea (—NH—CO—NH) | 2 | methyl | |
| 30 | urea (—NH—CO—NH) | 2 | butyl | 3.15(q); 2.55-2.25(m); 1.45-1.2(m); 0.9(t) |
| 31 | urea (—NH—CO—NH) | 2 | hexyl | |
| 32 | urea (—NH—CO—NH) | 2 | octadecyl | |
| 33 | urea (—NH—CO—NH) | 3 | methyl | |
| 34 | urea (—NH—CO—NH) | 3 | butyl | |
| 35 | urea (—NH—CO—NH) | 4 | methyl | |
| 36 | urea (—NH—CO—NH) | 4 | butyl | |
| 37 | urethane (—O—CO—NH—) | 2 | methyl | |
| 38 | urethane (—O—CO—NH—) | 2 | buthyl | 4.14(t); 3.22(q); 2.8(t); 2.6-2.3(m); 1.55-1.1(m); 0.93(t) |
| 39 | urethane (—O—CO—NH—) | 2 | hexyl | |
| 40 | urethane (—O—CO—NH—) | 2 | octadecyl | |
| 41 | urethane (—O—CO—NH—) | 3 | methyl | |
| 42 | urethane (—O—CO—NH—) | 3 | butyl | |
| 43 | urethane (—O—CO—NH—) | 4 | ethyl | |
| 44 | urethane (—O—CO—NH—) | 4 | butyl | |

TABLE 2

Chemico-physical characteristics of glycosaminoglycans (GAG) salts with the bases shown in TABLE 1.

| BASE N° | SALTS | GAG KIND | % GAG CONTENT (W/W° (1) | IR SPECTRUM (cm$^{-1}$) |
|---|---|---|---|---|
| 1 | 1a | P1 | 67 | 2960–2800, 2630, 1750, 1610, 1420, 1265, 1250, 1025. |
| 2 | 2a | " | 52, 6 | 2960–2800, 2630, 1750, 1610, 1420, 1265, 1250, 1025. |
| 3 | 3a | " | 53, 1 | 2960–2800, 2630, 1750, 1610, 1420, 1265, 1250, 1025. |
| 8 | 8a | " | 68, 8 | 2960–2800, 2630, 1750, 1610, 1420, 1265, 1250, 1025. |
| 15 | 15a | " | 68, 95 | 2960–2800, 1680, 1550, 1265, 1250, 1025. |
| 21 | 21a | " | 67, 28 | 2960–2800, 1680, 1550, 1265, 1250, 1025. |
| 41 (*) | 41a | " | 49, 9 | 2960–2800, 2630, 1750, 1610, 1420, 1265, 1250, 1025. |
| 1 | 1b | P2 | 67 | 2960–2800, 2630, 1750, 1610, 1420, 1250, 1265, 1025. |
| 2 | 2b | " | 52, 6 | 2960–2800, 2630, 1750, 1610, 1420, 1250, 1265, 1025. |
| 3 | 3b | " | 53, 1 | 2960–2800, 2630, 1750, 1610, 1420, 1250, 1265, 1025. |
| 8 | 8b | " | 68, 8 | 2960–2800, 2630, 1750, 1610, 1420, 1250, 1265, 1025. |
| 15 | 15b | " | 68, 95 | 2960–2800, 1680, 1550, 1265, 1250, 1025. |
| 21 | 21b | " | 67, 28 | 2960–2800, 1680, 1550, 1265, 1250, 1025. |
| 27 | 27b | " | 68, 1 | 2960–2800, 1680, 1550, 1265, 1250, 1025. |
| 33 | 33b | " | 66, 7 | 2960–2800, 2630, 1750, 1610, 1420, 1250, 1265, 1025 |
| 41 (*) | 41b | " | 49, 9 | 2960–2800, 2630, 1750, 1610, 1420, 1250, 1265, 1025. |
| 46 | 46b | " | 66, 4 | 2960–2800, 2630, 1750, 1610, 1420, 1250, 1265, 1025. |
| 1 | 1c | P3 | 73 | 2960–2800, 2630, 1750, 1680, 1610, 1550, 1420, 1265, 1250, 1025, 855. |
| 2 | 2c | " | 59, 8 | 2960–2800, 2630, 1750, 1680, 1610, 1550, 1420, 1265, 1250, 1025, 855. |

TABLE 2-continued

Chemico-physical characteristics of glycosaminoglycans (GAG) salts with the bases shown in TABLE 1.

| BASE N° | SALTS | GAG KIND | % GAG CONTENT (W/W°) (1) | IR SPECTRUM ($cm^{-1}$) |
|---|---|---|---|---|
| 8 | 8c | " | 74, 6 | 2960-2800, 2630, 1750, 1680, 1610, 1550, 1420, 1265, 1250, 1025, 855. |
| 15 | 15c | " | 74, 7 | 2960-2800, 1680, 1610, 1550, 1420, 1265, 1250, 1025, 855. |
| 21 | 21c | " | 73, 2 | 2960-2800, 1680, 1610, 1550, 1420, 1265, 1250, 1025, 855. |
| 41 (*) | 41c | " | 60, 8 | 2960-2800, 2630, 1750, 1610, 1420, 1265, 1250, 1025. |
| 1 | 1d | P4 | 68, 2 | 2960-2800, 2630, 1750, 1610, 1420, 1265, 1250, 1025. |
| 2 | 2d | " | 54 | 2960-2800, 2630, 1750, 1610, 1420, 1265, 1250, 1025. |
| 3 | 3d | " | 55, 1 | 2960-2800, 2630, 1750, 1610, 1420, 1265, 1250, 1025. |
| 8 | 8d | " | 69, 4 | 2960-2800, 2630, 1750, 1610, 1420, 1265, 1250, 1025. |
| 15 | 15d | " | 70 | 2960-2800, 2630, 1680, 1550, 1265, 1250, 1025 |
| 21 | 21d | " | 68, 4 | 2960-2800, 2630, 1680, 1550, 1265, 1250, 1025 |
| 1 | 1f | P5 | 65, 8 | 2960-2800, 2630, 1750, 1610, 1420, 1265, 1250, 1025. |
| 2 | 2f | " | 51, 2 | 2960-2800, 2630, 1750, 1610, 1420, 1265, 1250, 1025. |

(*) wherein $R_5 = R_6 = -CH_3$. (1) Said values - according to the batch and to the used salification method - may change of a ± 10% value - In the NMR spectra only the signals due to the base used in the salification may be observed. - The above reported spectral characteristics do not change using GAG of different kinds and batches. - The solubilities in water, alcohols and organic solvents depend on the substituents $R_1$, $R_2$, $R_3$, $R_4$, $R_7$ and $R_8$ and on the nature of X.

TABLE 3

| SALT N° | RAT | RABBIT |
|---|---|---|
| P1 | 0.01 ± 0.01 | 1 ± 0.5 |
| 1a | — | — |
| 2a | 4.5 ± 1.2 | 1.4 ± 0.5 |
| 3a | — | — |
| 4a | — | — |
| 8a | — | — |
| 15a | — | — |
| 21a | — | — |
| P2 | 2.6 ± 0.6 | 4.5 ± 0.6 |
| 1b | — | — |
| 2b | 24.0 ± 3.0 | 7.6 ± 1.1 |
| 3b | — | 5.5 ± 1.7 |
| 4b | — | — |
| 5b | — | 1.9 ± 1.1 |
| 7b | — | 12.5 ± 1.2 |
| 8b | — | — |
| 11b | — | 6.2 ± 1.5 |
| P4 | — | — |
| 1d | — | — |
| 2d | — | — |
| 3d | — | — |
| 8d | — | — |
| 15d | — | — |
| 21d | — | — |

TABLE 3a

| | | |
|---|---|---|
| p1 | — | |
| 2a | 9.1 ± 5.0 | |
| 3a | — | |
| 4a | — | |
| 8a | — | |
| 41a | — | |
| p2 | — | |
| 1b | — | |
| 2b | — | |
| 4b | — | |
| 21b | — | |
| p4 | — | |
| 2d | — | |
| 21d | — | |

TABLE 4

| SALT N° | DOSE mg/kg i.d. | RAT | RABBIT |
|---|---|---|---|
| p1 | 50 | 0.01 ± 0.01 | — |
| | 100 | — | 1.0 ± 0.5 |
| 2a | 50 | 0.4 ± 0.2 | — |
| | 100 | 4.5 ± 1.2 | 1.4 ± 0.5 |
| | 200 | 13.4 ± 3.0 | 8.0 ± 0.7 |
| p2 | 25 | — | 0.65 ± 0.65 |
| | 50 | 2.6 ± 0.6 | 2.4 ± 1.2 |
| | 100 | — | 4.5 ± 0.6 |
| 2b | 50 | 2.6 ± 0.7 | 1.7 ± 1.0 |
| | 100 | 24.0 ± 3.0 | 7.6 ± 1.1 |
| | 200 | 12.2 ± 3.0 | 23.8 ± 3.0 |
| 3b | 50 | — | 2.4 ± 2.2 |
| | 100 | — | 5.5 ± 1.7 |
| 7b | 50 | — | 2.8 ± 1.4 |
| | 100 | — | 12.5 ± 1.2 |

TABLE 5

| SALT N° | DOSE mg/kg i.d. | TIME min. | RAT | RABBIT |
|---|---|---|---|---|
| p1 | 50 | 0 | 0.03 ± 0.02 | — |
| | | 30 | 0.01 ± 0.01 | — |
| | | 60 | 0.4 ± 0.01 | — |
| | | 120 | 0.01 ± 0.01 | — |
| | 100 | 0 | — | 0.03 ± 0.03 |
| | | 30 | — | 1.0 ± 0.5 |
| | | 60 | — | 1.2 ± 0.2 |
| | | 120 | — | 0.03 ± 0.03 |
| | | 180 | — | 0.4 ± 0.1 |
| 2a | 100 | 0 | 0.03 ± 0.02 | — |
| | | 30 | 4.5 ± 1.2 | — |
| | | 60 | 6.9 ± 1.7 | — |
| | | 120 | 1.3 ± 0.5 | — |
| | 200 | 0 | — | 0.01 ± 0.01 |
| | | 30 | — | 8.0 ± 0.7 |
| | | 60 | — | 7.0 ± 1.1 |

TABLE 5-continued

| SALT N° | DOSE mg/kg i.d. | TIME min. | RAT | RABBIT |
|---|---|---|---|---|
| | | 120 | — | 3.2 ± 0.6 |
| | | 180 | — | 2.91 ± 1.0 |
| p2 | 50 | 0 | 0.03 ± 0.02 | 0.5 ± 0.4 |
| | | 30 | 2.6 ± 0.6 | 2.4 ± 1.2 |
| | | 60 | 2.7 ± 0.5 | 2.8 ± 2.0 |
| | | 120 | 0.6 ± 0.3 | 1.6 ± 1.5 |
| 3b | 100 | 0 | — | 0.2 ± 0.1 |
| | | 30 | — | 5.5 ± 1.7 |
| | | 60 | — | 5.5 ± 1.5 |
| | | 120 | — | 3.9 ± 1.0 |
| 2b | 100 | 0 | 0.1 ± 0.07 | 0.2 ± 0.1 |
| | | 30 | 24.0 ± 3.0 | 7.6 ± 1.1 |
| | | 60 | 15.0 ± 2.0 | 7.0 ± 1.2 |
| | | 120 | 11.8 ± 2.0 | 6.0 ± 1.3 |
| | | 180 | — | 7.5 ± 1.1 |
| 4b | 100 | 0 | | |
| | | 30 | | |
| | | 60 | | |
| | | 120 | | |
| 7b | 100 | 0 | — | 0.2 ± 0.2 |
| | | 30 | — | 12.5 ± 1.2 |
| | | 60 | — | 13.0 ± 2.9 |
| | | 120 | — | 11.4 ± 1.5 |
| 11b | 100 | 0 | — | 0.1 ± 0.1 |
| | | 30 | — | 6.3 ± 1.5 |
| | | 60 | — | 5.2 ± 1.6 |
| | | 120 | — | 3.9 ± 1.3 |
| 5b | 100 | 0 | — | 0.4 ± 0.2 |
| | | 30 | — | 1.9 ± 1.1 |
| | | 60 | — | 3.5 ± 1.3 |
| | | 120 | — | 2.9 ± 0.3 |

TABLE 6

| SALT N° | TIME min. | μg/ml |
|---|---|---|
| 2a | 0 | 0.2 ± 0.1 |
| | 30 | 26.4 ± 2.1 |
| | 60 | 20.0 ± 1.6 |
| | 120 | 19.9 ± 2.6 |
| | 180 | 18.0 ± 2.7 |
| | 240 | 12.4 ± 0.5 |

The present invention also relates to all the industrially applicable aspects connected with the use of salts of glycosaminoglycans with cations of formula I as therapeutic agents. Therefore, an essential object of the invention is provided by pharmaceutical compositions containing as the active ingredient therapeutically effective amounts of said salts together with conventional excipients and carriers.

Examples of said pharmaceutical compositions are tablets, sugar-coated pills, syrups, vials for oral, intramuscular or intravenous administrations and suppositories, containing 5 to 500 mg of the active ingredient, to be administered 1 to 3 times a day.

We claim:

1. Salts of glycosaminoglycans with cations of formula

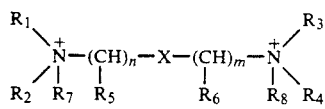

(I)

wherein:

$R_1$, $R_2$, $R_3$ and $R_4$, which are the same or different, represent hydrogen; linear or branched alkyl; or cycloalkyl;

$R_5$ and $R_6$, which are the same or different, represent hydrogen or $C_1$-$C_4$ alkyl;

$R_7$ and $R_8$, which are the same or different, represent hydrogen or $C_1$-$C_4$ alkyl;

n and m, which are the same or different, are integers 1 to 4 inclusive;

X represents:

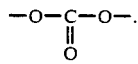

2. Salts according to claim 1 wherein the glycosaminoglycan is selected from the group consisting of:
unfractionated heparin;
heparinic fractions and fragments;
heparins, fractions and fragments thereof and supersulfated derivatives thereof;
dermatan sulfate, fragments and fractions thereof and supersulfated derivatives thereof;
heparan sulfate, fragments and fractions thereof and supersulfated derivatives thereof; and
N-desulfated heparins.

3. Salts according to claim 1, wherein anions are neutralized with inorganic or organic, pharmaceutically acceptable cations.

4. Salts according to claim 1, characterized in that any cations are neutralized with anions of inorganic or organic pharmaceutically acceptable acids.

5. Glycosaminoglycan salts of bases of formula Ia

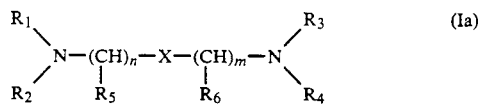

(Ia)

wherein $R_2$-$R_6$, X, m and n are as defined in claim 1 with the proviso that when $R_1$, $R_2$, $R_3$ and $R_4$ are methyl, n and m cannot be contemporaneously 2.

6. The salts of claim 5, wherein:
n=m =2; $R_1$=$R_2$=$R_3$=$R_4$ = butyl
n=m =2; $R_1$=$R_2$=$R_3$=$R_4$ = ethyl
n=m =2; $R_1$=$R_2$=$R_3$=$R_4$ = hexyl
n=m =3; $R_1$=$R_2$=$R_3$=$R_4$ = ethyl
n=m =3; $R_1$=$R_2$=$R_3$=$R_4$ = butyl
n=m =3; $R_1$=$R_2$=$R_3$=$R_4$ = hexyl
n=m =3; $R_1$=$R_2$=$R_3$=$R_4$ = ethyl
n=m =3; $R_1$=$R_2$=$R_3$=$R_4$ = butyl
n=m =4; $R_1$=$R_2$=$R_3$=$R_4$ = hexyl 7. The salts of claim 6 wherein the glycosaminoglycans are selected from the group consisting of:
unfractionated heparin;
heparinic fractions and fragments;
heparins, fractions and fragments thereof and supersulfated derivatives thereof;
dermatan sulfate, fragments and fractions thereof and supersulfated derivatives thereof; and
N-desulfated heparins.

8. The salts of claim 6, wherein $R_5$ and $R_6$ are hydrogen; n = m is 2, 3 or 4; $R_1$, $R_2$, $R_3$, and $R_4$, which are the same, represent n-butyl or n-hexyl; and the glycosaminoglycans are selected from the group consisting of unfractionated heparin and heparin fractions.

9. Pharmaceutical compositions containing as the active principle a salt of claim 1 and a pharmaceutically acceptable carrier.

10. Pharmaceutical compositions according to claim 9 in oral or rectal administration form.

* * * * *